US006629923B2

(12) United States Patent
Leysieffer

(10) Patent No.: US 6,629,923 B2
(45) Date of Patent: Oct. 7, 2003

(54) AT LEAST PARTIALLY IMPLANTABLE HEARING SYSTEM WITH DIRECT MECHANICAL STIMULATION OF A LYMPHATIC SPACE OF THE INNER EAR

(75) Inventor: Hans Leysieffer, Taufkirchen (DE)

(73) Assignee: Phonak AG, Stafa (CH)

( * ) Notice: Subject to any disclaimer, the term of this patent is extended or adjusted under 35 U.S.C. 154(b) by 39 days.

(21) Appl. No.: 09/956,936

(22) Filed: Sep. 21, 2001

(65) Prior Publication Data

US 2002/0035309 A1 Mar. 21, 2002

(30) Foreign Application Priority Data

Sep. 21, 2000 (DE) ........................................ 100 46 938

(51) Int. Cl.[7] .......................... H04R 25/00; A61N 1/10
(52) U.S. Cl. ........................................... 600/25; 607/57
(58) Field of Search ........................ 600/25; 607/55–57, 607/137, 27, 37; 381/23.1, 312; 128/903

(56) References Cited

U.S. PATENT DOCUMENTS

| | | | |
|---|---|---|---|
| 3,557,775 | A | 1/1971 | Mahoney |
| 3,712,962 | A | 1/1973 | Epley |
| 3,764,748 | A | 10/1973 | Branch et al. |

(List continued on next page.)

FOREIGN PATENT DOCUMENTS

| | | |
|---|---|---|
| DE | 42 21 866 | 1/1994 |
| DE | 196 38 158 | 4/1998 |
| EP | 0 190 836 | 8/1986 |
| EP | 0 263 254 | 4/1988 |
| EP | 0 400 630 | 12/1990 |
| EP | 0 499 940 | 8/1992 |
| EP | 0 537 385 | 4/1993 |
| WO | WO 90/07251 | 6/1990 |
| WO | WO 96/34508 | 10/1996 |
| WO | WO 97/18689 | 5/1997 |

OTHER PUBLICATIONS

Zenner et al., “First Implantations of a Totally Implantable Electronic Hearing System for Sensorineural Hearing Loss”, pp. 844–852, 1998, HNO vol. 46.

Leysieffer et al., “A Totally Implantable Hearing Device for the Treatment of Sensorineural Hearing Loss: TICA LZ 3001”, pp. 853–863, 1998, HNO vol. 46.

Yanagihara et al., “Implantable Hearing Aid”, pp. 869–872, Aug. 1987, Arch Otolaryngol Head Neck Surg—vol. 113.

Zenner et al., “Active Electronic Hearing Implants for Patients with Conductive and Sensorineural Hearing Loss—A New Era of Ear Surgery”, pp. 749–774, 1997, HNO vol. 45.

Zenner et al., “Totally Implantable Hearing Device for Sensorineural Hearing Loss”, p. 1751, 1998, The Lancet vol. 352, No. 9142.

Müller–Deile et al., “Cochlear Implant Supply for Non–Deaf Patients?”, pp. 136–143, 1998, Laryngo–Rhino–Otol., vol. 77.

(List continued on next page.)

*Primary Examiner*—Eric F. Winakur
*Assistant Examiner*—Nikita R Veniaminov
(74) *Attorney, Agent, or Firm*—Nixon Peabody LLP; David S. Safran

(57) ABSTRACT

An at least partially implantable sensor for rehabilitation of a hearing disorder having at least one acoustic sensor for picking up acoustic sensor signals and converting the acoustic sensor signals into corresponding electrical audio sensor signals; an electronic signal processing unit for audio signal processing and amplification of the electric sensor signals; an electrical power supply unit which supplies individual components of the system with energy, and an actoric output arrangement for direct mechanical stimulation of a lymphatic inner ear space, wherein the actoric output arrangement has an intracochlear electromechanical transducer.

29 Claims, 5 Drawing Sheets

U.S. PATENT DOCUMENTS

| | | | | | |
|---|---|---|---|---|---|
| 4,352,960 | A | | 10/1982 | Dormer et al. | |
| 4,441,210 | A | | 4/1984 | Hochmair et al. | |
| 4,894,728 | A | * | 1/1990 | Goodman | 360/6 |
| 4,947,432 | A | * | 8/1990 | Topholm | 381/315 |
| 4,988,333 | A | | 1/1991 | Engebretson et al. | |
| 4,989,251 | A | * | 1/1991 | Mangold | 381/314 |
| 5,015,224 | A | | 5/1991 | Maniglia | |
| 5,015,225 | A | | 5/1991 | Hough et al. | |
| 5,070,535 | A | | 12/1991 | Hochmair et al. | |
| 5,095,904 | A | | 3/1992 | Seligman et al. | |
| 5,271,397 | A | | 12/1993 | Seligman et al. | |
| 5,277,694 | A | | 1/1994 | Leysieffer et al. | |
| 5,279,292 | A | | 1/1994 | Baumann et al. | |
| 5,360,388 | A | | 11/1994 | Spindel et al. | |
| 5,411,467 | A | | 5/1995 | Hortmann et al. | |
| 5,531,787 | A | * | 7/1996 | Lesinski et al. | 623/10 |
| 5,581,747 | A | * | 12/1996 | Anderson | 713/400 |
| 5,597,380 | A | | 1/1997 | McDermott et al. | |
| 5,601,617 | A | | 2/1997 | Loeb et al. | |
| 5,603,726 | A | | 2/1997 | Schulman et al. | |
| 5,624,376 | A | | 4/1997 | Ball et al. | |
| 5,626,629 | A | | 5/1997 | Faltys et al. | |
| 5,772,575 | A | | 6/1998 | Lesinski et al. | |
| 5,795,287 | A | | 8/1998 | Ball et al. | |
| 5,814,095 | A | | 9/1998 | Müller et al. | |
| 5,881,158 | A | * | 3/1999 | Lesinski et al. | 381/174 |
| 5,951,601 | A | | 9/1999 | Lesinski et al. | |
| 5,977,689 | A | | 11/1999 | Neukermans | |
| 5,984,859 | A | | 11/1999 | Lesinski | |
| 5,999,632 | A | | 12/1999 | Leysieffer et al. | |
| 6,068,589 | A | | 5/2000 | Neukermanns | |
| 6,092,422 | A | * | 7/2000 | Binnig et al. | 73/651 |
| 6,131,581 | A | | 10/2000 | Leysieffer et al. | |
| 6,161,046 | A | * | 12/2000 | Maniglia et al. | 607/57 |
| 6,198,971 | B1 | | 3/2001 | Leysieffer | |
| 6,251,062 | B1 | | 6/2001 | Leysieffer | |
| 6,259,951 | B1 | * | 7/2001 | Kuzma et al. | 607/57 |
| 6,368,267 | B1 | * | 4/2002 | Lenhardt | 600/25 |
| 6,381,336 | B1 | * | 4/2002 | Lesinski et al. | 381/326 |
| 6,415,186 | B1 | * | 7/2002 | Chim et al. | 607/57 |
| 6,473,651 | B1 | * | 10/2002 | Kuzma et al. | 607/57 |
| 6,496,734 | B1 | * | 12/2002 | Money | 607/56 |

OTHER PUBLICATIONS

Lehnhardt, "Intracochlear Placement of Cochlear Implant Electrodes in Soft Surgery Technique", pp. 356–359, 1993, HNO vol. 41.

Ruh et al., "Cochlear Implant for Patients with Residual Hearing", pp. 347–350, 1997, Laryngo–Rhino–Otol. vol. 76.

* cited by examiner

AT LEAST PARTIALLY IMPLANTABLE HEARING SYSTEM WITH DIRECT MECHANICAL STIMULATION OF A LYMPHATIC SPACE OF THE INNER EAR

BACKGROUND OF THE INVENTION

1. Field of the Invention

This invention relates to an at least partially implantable system for rehabilitation of a hearing disorder comprising at least one acoustic sensor for picking up acoustic sensor signals and converting them into corresponding electrical audio sensor signals, an electronic signal processing unit for audio signal processing and amplification of the electrical sensor signals, an electrical power supply unit which supplies individual components of the system with energy, and an actoric output arrangement for direct mechanical stimulation of a lymphatic inner ear space.

2. Description of Related Art

The term "hearing disorder" is defined here as including all types of inner ear damages, combined inner ear and middle ear damages, and a temporary or permanent noise impression (tinnitus).

In recent years, rehabilitation of sensorineural hearing disorders with partially implantable electronic systems has acquired major importance. In particular, this applies to the group of patients in which hearing has completely failed due to accident, illness or other effects or in which hearing is congenitally non-functional. If, in these cases, only the inner ear (cochlea), and not the neural auditory path which leads to the brain, is affected, the remaining auditory nerve can be stimulated with electrical stimulation signals. Thus, a hearing impression can be produced which can lead to speech comprehension. In these so-called cochlear implants (CI), an array of stimulation electrodes, which is controlled by an electronic system (electronic module), is inserted into the cochlea. This electronic module is encapsulated with a hermetic, biocompatible seal and is surgically embedded in the bony area behind the ear (mastoid). The electronic system contains essentially only decoder and driver circuits for the stimulation electrodes. Acoustic sound reception, conversion of this acoustic signal into electrical signals and their further processing, always takes place externally in a so-called speech processor which is worn outside on the body. The speech processor converts the preprocessed signals into a correspondingly coded high frequency carrier signal which, via inductive coupling, is transmitted through the closed skin (transcutaneously) to the implant. The sound-receiving microphone is always located outside of the body and, in most applications, in a housing of a behind-the-ear hearing aid worn on the external ear. The microphone is connected to the speech processor by a cable. Such cochlear implant systems, their components, and the principles of transcutaneous signal transmission are described, by way of example, in U.S. Pat. Nos. 5,070,535, 4,441,210 and 5,626,629. Processes of speech processing and coding in cochlear implants are described, for example, in Published European Patent Application EP 0 823 188 A1, in European Patent EP 0 190 836 A1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time there have been approaches to offer better rehabilitation than with conventional hearing aids to patients with a sensorineural hearing disorder which cannot be surgically corrected by using partially or totally implantable hearing aids. The principle consists, in most embodiments, in stimulating an ossicle of the middle ear or, directly, the inner ear via mechanical or hydromechanical stimulation and not via the amplified acoustic signal of a conventional hearing aid in which the amplified acoustic signal is supplied to the external auditory canal. The actuator stimulus of these electromechanical systems is accomplished with different physical transducer principles such as, for example, by electromagnetic and piezoelectric systems. The advantage of these devices is seen mainly in the sound quality which is improved compared to conventional hearing aids, and, for totally implanted systems, in the fact that the hearing prosthesis is not visible.

Such partially and totally implantable electromechanical hearing aids have been described, for example, by Yanigahara and Suzuki et al. in Arch Otolaryngol Head Neck, Surg-Vol 113, August 1987, pp. 869–872; Hoke M. (ed.), in Advances in Audiology, Vol. 4, Karger Basel, 1988), H. P. Zenner et al. "First implantations of a totally implantable electronic hearing system for sensorineural hearing loss", in HNO Vol. 46, 1998, pp. 844–852; H. Leysieffer et al. "A totally implantable hearing device for the treatment of sensorineural hearing loss: TICA LZ 3001", in HNO Vol. 46, 1998, pp. 853–863; H. P. Zenner et al. "Active electronic hearing implants for patients with conductive and sensorineural hearing loss—a new era of ear surgery" HNO 45, 1997, pp. 749–774; H. P. Zenner et al. "Totally implantable hearing device for sensorineural hearing loss", The Lancet Vol. 352, No. 9142, page 1751. Such hearing aids are also described in numerous patent documents among others in Published European Patent Applications EP 0 263 254 A1, EP 0 400 630 A1, and EP 0 499 940 A1, and in U.S. Pat. Nos. 3,557,775, 3,712,962, 3,764,748, 5,411,467, 4,352,960, 4,988,333, 5,015,224, 5,015,225, 5,360,388, 5,772,575, 5,814,095, 5,951,601, 5,977,689 and 5,984,859. The insertion of an electromechanical transducer through an opening in the promontory for direct fluid stimulation in the inner ear is described in U.S. Pat. Nos. 5,772,575, 5,951,601, 5,977,689 and 5,984,859.

Recently, partially and fully implantable hearing systems for rehabilitation of inner ear damage have been in clinical use. Depending on the physical principle of the output-side electromechanical transducer, and especially the type of coupling the transducer to the ossicle of the middle ear, it happens that the attained results of improving speech understanding can be very different. In addition, for many patients, a sufficient loudness level cannot be reached. This aspect is spectrally very diverse; this can mean that, at medium and high frequencies, for example, the generated loudness is sufficient, but not at low frequencies, or vice versa. Furthermore the spectral bandwidth which can be transmitted can be limited, thus, for example, to low and medium frequencies for electromagnetic transducers and to medium and high frequencies for piezoelectric transducers. In addition, nonlinear distortions, which are especially pronounced in electromagnetic transducers, can have an adverse effect on the resulting sound quality. The lack of loudness leads especially to the fact that the audiological indication range for implantation of an electromechanical hearing system is very limited. This means that patients, for example, with sensorineural hearing loss of greater than 50 dB ES (hearing loss) in the low tone range can only be inadequately supplied with a piezoelectric system. Conversely, pronounced high tone losses can only be poorly supplied with electromagnetic transducers.

Many patients with inner ear damage also suffer from temporary or permanent noise impressions (tinnitus) which cannot be surgically corrected and for which, to date, there are no approved drug treatments. Therefore, so-called tinnitus maskers (International Patent Application Publication WO-A 90/07251, published European Patent Application EP 0 537 385 A1, German Utility Model No. 296 16 956) are known. These devices are small, battery-driven devices which are worn like a hearing aid behind or in the ear and which, by means of artificial sounds which are emitted into the auditory canal, for example, via a hearing aid speaker, psychoacoustically mask the tinnitus, and thus, reduce the disturbing noise impression, if possible, to below the threshold of perception. The artificial sounds are often narrowband noise (for example, third-band noise). The spectral position and the loudness level of the noise can be adjusted via a programming device to enable adaptation to the individual tinnitus situation as optimally as possible. In addition, the so-called retraining method has been developed recently in which, by combination of a mental training program and presentation of broadband sound (noise) near the auditory threshold, the perceptibility of the tinnitus in quiet conditions is likewise supposed to be largely suppressed (H. Knoer "Tinnitus retraining therapy and hearing acoustics" journal "Hoerakustik" 2/97, pages 26 and 27). These devices are also called "noisers".

In the two aforementioned methods for hardware treatment of tinnitus, hearing aid-like, technical devices must be carried visibly outside on the body in the area of the ear. These devices stigmatize the wearer and, therefore, are not willingly worn.

U.S. Pat. No. 5,795,287 describes an implantable tinnitus masker with "direct drive" of the middle ear, for example, via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned, co-pending U.S. patent applications Ser. Nos. 09/372,172 and 09/468,860, which are hereby incorporated by reference, implantable systems for treatment of tinnitus by masking and/or noiser functions are described, in which the signal-processing electronic path of a partially or totally implantable hearing system is supplemented by corresponding electronic modules, such that the signals necessary for tinnitus masking or noiser functions can be fed into the signal processing path of the hearing aid function and the pertinent signal parameters can be individually adapted to the pathological requirements by further electronic measures. This adaptability can be accomplished by storing or programming the necessary setting data of the signal generation and feed electronics by using hardware and software in the same physical and logic data storage area of the implant system, and by controlling the feed of the masker or noiser signal into the audio path of the hearing implant via corresponding electronic regulating means.

The above described at least partially implantable hearing systems for rehabilitation of inner ear damage, which are based on an output-side electromechanical transducer, differ from conventional hearing aids essentially only in that the output-side acoustic stimulus (i.e., an amplified acoustic signal in front of the eardrum) is replaced by an amplified mechanical stimulus of the middle ear or inner ear. The acoustic stimulus of a conventional hearing aid ultimately leads to vibratory, i.e., mechanical, stimulation of the inner ear, via mechanical stimulation of the eardrum and the subsequent middle ear. The requirements for effective audio signal preprocessing are fundamentally similar or the same. Furthermore, in both embodiments on the output side a localized vibratory stimulus is ultimately routed to the damaged inner ear (for example, an amplified mechanical vibration of the stapes in the oval window of the inner ear).

For the aforementioned reasons, up to now implantable electromechanical systems cannot be employed for hearing disorders which approach deafness. Here cochlear implants with purely electrical stimulation of the inner ear may be considered which of course do not promise sound quality which for example would enable acceptable music transmission, but which rather are primarily designed for acquiring or restoring sufficient speech comprehension, as much as possible without lip reading. As a result of the electrical stimulation, as described, hearing losses which extend to complete deafness are possible in a spectrally wide audiological range.

In the case of a widely spread middle ear damage, the so-called otosclerosis, in which particularly the moveability of the ligament of the stapes suspension within the oval window is limited or completely prevented by calcareous degeneration, a passive prosthesis is used in an operation method called stapedotomy. On the one hand, this passive prosthesis is fixed by a bracket mostly to the long process of the incus; on the other hand, a usually cylindrical shaft of the prosthesis is inserted into an artificial opening in the footplate of the stapes. The stapes likewise may be completely removed. The oscillations of the tympanic membrane are transmitted by the malleus to the incus and thus cause corresponding oscillations of the passive prosthesis which result in dynamic volume displacements in the perilymph of the inner ear thereby evoking travelling waves on the basilar membrane and finally in a hearing impression. For decades this method has been very safely and successfully used as a reconstructive middle ear operation. The opening in the footplate of the stapes is made with the aid of fine surgical instruments or particularly by laser techniques.

Recently it has become scientifically known from CI implantations that even for incomplete deafness cochlear implants (CIs) can be successfully used when sufficient speech discrimination can no longer be achieved with a conventional hearing aid. Interestingly it was demonstrated that the important inner ear structures which enable residual acoustic hearing capacity can be maintained in part or largely stably over time when a CI electrode is inserted into the cochlea (S. Ruh et al.: "Cochlear implant for patients with residual hearing", Laryngo-Rhino-Otol. 76 (1997) 347–350; J. Mueller-Deile et al.: "Cochlear implant supply for non-deaf patients?" Laryngo-Rhino-Otol. 77 (1998) 136–143; E. Lehnhardt: "Intracochlear placement of cochlear implant electrodes in soft surgery technique", HNO 41 (1993), 356–359). In the foreseeable future it certainly will be possible, in case of residual hearing capacity, to clinically place CI electrodes intracochlearly in a manner such that the remaining inner ear structures can be preserved over the long term and thus can continue to be stimulated in a biologically proper manner, i.e. vibrationally, and lead to a usable hearing impression.

Commonly owned, co-pending U.S. patent application Ser. No. 09/833,704 which hereby is incorporated by reference, describes a hearing system comprising a plurality of electromechanical transducers which are distributed along the cochlea for stimulating the fluid filled inner ear spaces by generating travelling waves on the basilar membrane. Commonly owned, co-pending U.S. patent application Ser. No. 09/833,643 which hereby is incorporated by reference, describes a hearing system comprising a dual intracochlear arrangement which in combination comprises a stimulating arrangement having at least one stimulator element for an at least indirect mechanical stimulation of the inner ear and an electrically operative stimulating electrode arrangement having at least one cochlea implant electrode for an electric stimulation of the inner ear. These hearing systems require relatively complicated surgical interventions.

U.S. Pat. No. 5,977,689 describes a microactuator for a hearing system having a hollow body which is adapted for implantation in the middle ear and is filled with an incompressible liquid. At least one piezoelectric transducer, which is connected to a membrane and has a relatively large surface, is disposed within this hollow body. The interior of the hollow body communicates with a nozzle which is inserted into an artificial fenestration in the promontory and which is closed at its end remote from the hollow body by a membrane which is small relative to the transducer membrane. When corresponding electrical signals are supplied to the transducer, the latter applies a force on the liquid within the hollow body whereby the small membrane which closes the nozzle and is in contact with fluid in the inner ear, is deflected.

U.S. Pat. Nos. 5,772,575 and 5,984,859 disclose an implantable system for rehabilitation of a hearing disorder comprising microphone for picking up acoustic signals and converting them into corresponding electrical audio sensor signals, an electronic signal processing unit for audio signal processing and amplification of the electrical sensor signals, an electrical power supply unit which supplies individual components of the system with energy, and an actoric output unit for direct mechanical stimulation of a lymphatic inner ear space. The actoric output unit is in the form of a microactuator having a plane flexible membrane The microactuator membrane defines the front face of a screw which is screwed into an artificial fenestration in the promontory, or the microactuator is directly inserted into such a fenestration so that its plane membrane contacts fluid in the inner ear. In conformity with a further embodiment the microactuator is disposed in the shaft of a passive stapedotomy prosthesis of the above described type to provide for a combined passive and active stimulation.

SUMMARY OF THE INVENTION

A primary object of the present invention is to devise an at least partially implantable hearing system for rehabilitation of a hearing disorder which permits an improved rehabilitation of sensorineural hearing disorders.

This object is achieved by an at least partially implantable system for rehabilitation of a hearing disorder comprising at least one acoustic sensor for picking up acoustic sensor signals and converting the acoustic sensor signals into corresponding electrical audio sensor signals; an electronic signal processing unit for audio signal processing and amplification of the electrical sensor signals; an electrical power supply unit which supplies individual components of the system with energy; and an actoric output arrangement for direct mechanical stimulation of a lymphatic inner ear space, wherein said actoric output arrangement consists of an intracochlear electromechanical transducer.

The intracochlear transducer structure used in conformity with the subject invention has the particular advantage that the mechanical stimulus can be generated on the basis of a relatively large surface directly within the inner ear without any additional masses, suspension stiffnesses and/or lossy joints of the middle ear ossicles being disposed within the mechanical transmission path, which particularly could cause linear distortions of the transducer frequency characteristic to be transmitted. Furthermore it is to be expected that the direct inner ear stimulation leads to a substantially improved interindividual reproducibility of the mechanical stimulation when compared to a transmission via coupling elements to the middle ear ossicles, because in the latter case anatomic variations and particularly the individual proceedings applied by the surgeon always play an important role.

A further advantage of the subject invention is that the occurrence of feedback (feeding back of the output signal to the sound sensor (microphone)) may be expected to be substantially reduced because an excitation of the ossicular chain and therefore of the tympanic membrane to oscillate is distinctly reduced or avoided. This is of particular advantage when a sound sensor (microphone function) is disposed in the immediate vicinity of the tympanic membrane (German Patent No. 196 38 158 and U.S. Pat. No. 5,999,632).

The presently used electromechanical transducer preferably operates according the principle of dynamic volume change as a result of dynamic surface enlargement or reduction of the transducer in conformity with an electrical AC signal controlling the transducer. An optimized effect of the transducer may be expected when the design is selected such that essentially the entire surface of the intracochlear transducer oscillates (ideal ball-type oscillator) because this provides for a maximized volume displacement and thus a maximized stimulation level at a given controlling energy for the transducer as determined by the preprocessing electronic system.

The operative access for the intracochlear transducer preferably is through the oval window or an artificial cochlear window, such as a promontory window. In view of the fact that, as discussed above, the stapedotomy in the course of which an opening is formed in the footplate of the stapes, for a long time has proved to be a safe middle ear operation, it is to be expected that such an opening step and thus a direct access to the inner ear is possible without any increased risk even if there is no otosclerosis and the footplate still is fully movable, that is if there is a pure inner ear hearing impairment. This means that proven operation techniques of the stapedotomy can be transferred to the implantation of the transducer used according to the invention.

Preferably, the intracochlear transducer is disposed at an end of a flexible carrier structure, particularly a polymeric carrier structure.

The approach of the subject invention basically may be utilized in connection with all known transducer principles, such as electromagnetic, electrodynamic, piezoelectric, dielectric (capacitive) and magnetostrictive transducer principles. The piezoelectric principle is particularly suited because the ideal of a surface oscillator may be approached thereby in a particularly easy manner using a simple transducer design. Particularly, the intracochlear transducer may be designed so as to provide, at a given transducer voltage, for a maximum change of volume at a minimum of electrical power input, wherein preferably use is made of geometrical shape transformations, particularly of the bimorphic principle, of the unimorphic principle or of the heteromorphic principle with passive material partners.

The intracochlear transducer can be manufactured in a particularly simple manner and can be easily implanted, when it comprises a piezoelectric tube section of cylindrical cross-section, the inner and outer circumferential surfaces thereof having metal coatings thereon which define electrical transducer electrodes.

The intracochlear piezoelectric transducer may be made on the basis of a lead-zirconate-titanate material. Particularly suited also is a single- or multi-layer coil of a thin polyvinylidene fluoride (PVDF) foil. Preferably, the transducer element is provided with a biocompatible cover, preferably made of an elastic polymer, for example silicone. The entire transducer element may be enclosed by such a biocompatible cover. In conformity with a modified embodiment, the cover has at least one opening, and preferably at least two openings at the lower end of the tube and within the upper region of the cover, for entry and exit of intracochlear lymph. The opening or openings is (are) preferably dimensioned such that a dynamic change of the radius of the transducer directly results in a displacement of lymph and thus in an intracochlear volume displacement. Particularly, the tube surface of the intracochlear transducer and the cross-sectional area of the inlet and outlet openings may be dimensioned to provide for a hydraulic transformation such that higher lymph velocities and consequently higher cochlea stimulation levels are attained than those obtained by a direct surface change of the transducer itself.

Preferably, the transducer, as is known per se from U.S. Pat. No. 5,277,694, has a first mechanical resonance frequency which is at the upper spectral end of the transmission range. In case of a voltage impression onto a, for example piezoelectric, transducer this results in a flat frequency characteristic, whereby linear distortions are avoided to a large extent. The intracochlear transducer preferably may have a transmission range from about 100 cps to about 10,000 cps.

In conformity with a further embodiment of the invention a mechanical attenuation element may be provided for decoupling the oscillations of the intracochlear transducer from a transducer feed line to thereby prevent or substantially reduce an at least partial co-oscillation of the middle ear ossicles caused by a mechanical contact with this feed line. Otherwise, such a co-oscillation could lead to disturbing feedback when using sensors (microphones) disposed close to the tympanic membrane. Preferably, the material of the mechanical attenuation element is selected so as to provide—at a similar cross-sectional geometry as that of the carrier—for a large mechanical impedance difference as compared to the material of the carrier in order to achieve high attenuation values.

The intracochlear transducer preferably may be dimensioned to obtain volumetrical changes of about 2–10 microliters. The total diameter of the intracochlear transducer arrangement advantageously is within a range from 0.2 mm to 2.0 mm, and the depth of immersion and the length of the active transducer element of the intracochlear transducer preferably may be from 0.3 mm to 2 mm.

According to an embodiment of the invention the system comprises a digital signal processor for processing the audio sensor signals and/or for generating digital signals for tinnitus masking.

The signal processor can be designed to be static such that as a result of scientific findings respective software modules are filed once in a program storage of the signal processor and remain unchanged. But then if later, for example due to more recent scientific findings, improved algorithms for signal processing are available and these improved algorithms are to be used, the entire implant or the implant module which contains the corresponding signal processing unit must be replaced by a new unit comprising the altered operating software by invasive surgery on the patient. This surgery entails renewed medical risks for the patient and is very complex. This problem can be solved in that, in another embodiment of the invention, the system comprises telemetry means, preferably computer (PC) based telemetry means, for transmitting data between an implanted portion of the system and an external unit, and that a rewritable implantable storage arrangement is assigned to the signal processor for storage and retrieval of an operating program, wherein at least parts of the operating program are adapted to be changed or replaced by data transmitted via the telemetry means. In this way, after implantation of the implantable system, the operating software as such, inclusive of software for controlling the intracochlear transducer, can be changed or completely replaced, as is explained for otherwise known systems for rehabilitation of hearing disorders in commonly owned U.S. Pat. No. 6,198,971 which is hereby incorporated by reference. This permits an implementation of further scientific findings in the implant, for example as to speech signal processing strategies, without requiring an exchange of the implant by surgery.

Preferably, the design is such that, in addition, for fully implantable systems, in a manner known per se, operating parameters, i.e., patient-specific data, for example, audiological adaptation data, or variable implant system parameters (for example, as a variable in a software program for controlling the intracochlear transducer or for control of battery recharging) can be transmitted transcutaneously into the implant after implantation, i.e., wirelessly through the closed skin, and thus, can be changed. In such an embodiment, preferably, the software modules are designed to be dynamic or reprogrammable to provide for an optimum rehabilitation of the respective hearing disorder. In particular, the software modules can be designed to be adaptive, and parameter adaption can be done by training by the implant wearer and optionally by using other aids.

Furthermore, the signal processing electronics can contain a software module which achieves stimulation as optimum as possible based on an adaptive neural network. Training of this neural network can take place again by the implant wearer and/or using other external aids.

The storage arrangement for storage of operating parameters and the storage arrangement for storage and retrieval of the operating program can be implemented as storages independent of one another; however there can also be a single storage in which both the operating parameters and also operating programs can be filed.

The subject approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (intracochlear transducer) biological interfaces are always dependent on anatomic, biological and neurophysiological circumstances, for example on the interindividual healing process. These interface parameters can also be individual, especially time-variant. Thus, for example the transmission behavior of an implanted microphone can vary interindividually and individually as a result of being covered by tissue, and the transmission behavior of the intracochlear electromechanical transducer which is coupled to the inner ear can vary interindividually and individually in view of different coupling qualities. These differences of interface parameters, which cannot be eliminated or reduced in the devices known from the prior art even by replacing the implant, now can be optimized by changing or improving the signal processing of the implant.

In an at least partially implantable hearing system, it can be advisable or become necessary to implement signal processing algorithms which have been improved after implantation. Especially the following should be mentioned here:

speech analysis processes (for example, optimization of a fast Fourier transform (FFT)), static or adaptive noise detection processes, static or adaptive noise suppression processes, processes for optimization of the signal to noise ratio within the system, optimized signal processing strategies in progressive hearing disorder, output level-limiting processes for protection of the patient in case of implant malfunctions or external faulty programming, processes of preprocessing of several sensor (microphone) signals, especially for binaural positioning of the sensors, processes for binaural processing of two or more sensor signals in binaural sensor positioning, for example optimization of spacial hearing or spacial orientation, phase or group delay time optimization in binaural signal processing, processes for optimized driving of the output stimulators, especially in the case of binaural positioning of the stimulators.

Among others, the following signal processing algorithms can be implemented with this system even after implantation:

processes for optimization of the operating behavior of the intracochlear output transducer (for example, optimization of the frequency response and phase response, improvement of the impulse response), speech signal compression processes for sensorineural hearing loss, signal processing methods for recruitment compensation in sensorineural hearing loss.

Furthermore, in implant systems with a secondary power supply unit, i.e., a rechargeable battery system, but also in systems with primary battery supply it can be assumed that these electrical power storage units will enable longer and longer service lives and thus increasing residence times in the patients as technology advances. It can be assumed that fundamental and applied research for signal processing algorithms will make rapid progress. The necessity or the patient's desire for operating software adaptation and modification will therefore presumably take place before the service life of the implanted power source expires. The system described here allows this adaptation of the operating programs of the implant even when the implant has already been implanted.

Preferably, there can furthermore be provided a buffer storage arrangement in which data transmitted from the external unit via the telemetry means can be buffered before being relayed to the signal processor. In this way the transmission process from the external unit to the implanted system can be terminated before the data transmitted via the telemetry means are relayed to the signal processor.

Furthermore, there can be provided checking logic which checks the data stored in the buffer storage arrangement before relaying the data to the signal processor. There can be provided a microprocessor module, especially a microcontroller, for control of the signal processor within the implant via a data bus, preferably the checking logic and the buffer storage arrangement being implemented in the microprocessor module, wherein also program parts or entire software modules can be transferred via the data bus and the telemetry means between the outside world, the microprocessor module and the signal processor.

An implantable storage arrangement for storing a working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be done.

Analogously to the above, the buffer storage arrangement can also comprise at least two storage areas for storage and retrieval of data transferred from the external unit via the telemetry means, so that after data transmission from the external unit still in the area of the buffer storage the absence of errors in the transferred data can be checked. The storage areas can be designed for example for complementary filing of the data transferred from the external unit. At least one of the storage areas of the buffer storage arrangement, however, can also be designed to store only part of the data transferred from the external unit, wherein in this case the absence of errors in the transferred data is checked in sections.

Furthermore, to ensure that in case of transmission errors, a new transmission process can be started, a preprogrammed read-only memory area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit but also for transfer of operating parameters between the implantable part of the system and the external unit such that on the one hand such parameters (for example the volume) can be adjusted by a physician, a hearing aid acoustics specialist or the wearer of the system himself, and on the other hand the system can also transfer the parameters to the external unit, for example to check the status of the system.

A totally implantable hearing system of the aforementioned type can have on the implant side in addition to the intracochlear transducer and the signal processing unit at least one implantable acoustic sensor and a rechargeable electrical storage element, and in this case a wireless transcutaneous charging device can be provided for charging of the storage element. For a power supply there can also be provided a primary cell or another power supply unit which does not require transcutaneous recharging. This applies especially when it is considered that in the near future, mainly by continuing development of processor technology, a major reduction in power consumption for electronic signal processing can be expected so that for implantable hearing systems new forms of power supply will become usable in practice, for example power supply which uses the Seebeck effect, as is described in U.S. Pat. No. 6,131,581. Preferably, there is also provided a wireless remote control for control of the implant functions by the implant wearer.

In case of a partially implantable hearing system, at least one acoustic sensor, the electronic signal processing unit, the power supply unit and a modulator/transmitter unit are contained in an external module which can be worn outside on the body, especially on the head over the implant. The implant comprises the output-side electromechanical intracochlear transducer, but is passive in terms of energy and receives its operating energy and control data for the intracochlear transducer via the modulator/transmitter unit in the external module.

The described system can be designed to be monaural or binaural for the fully implantable design as well as for the partially implantable design. A binaural system for rehabilitation of a hearing disorder of both ears has two system units which each are assigned to one of the two ears. In doing so the two system units can be essentially identical to one another. However, one of the system units can also be designed as a master unit and the other system unit as a slave unit which is controlled by the master unit. The signal processing modules of the two system units can communicate with one another in any way, especially via a wired implantable line connection or via a wireless connection, preferably a bidirectional high frequency path, an ultrasonic path coupled by bone conduction, or a data transmission path which uses the electrical conductivity of the tissue of the implant wearer, such that in both system units optimized binaural signal processing and transducer control are achieved.

These and further objects, features and advantages of the present invention will become apparent from the following description when taken in connection with the accompanying drawings which, for purposes of illustration only, shows several embodiments in accordance with the present invention.

DETAILED DESCRIPTION OF THE INVENTION

Figure 1:
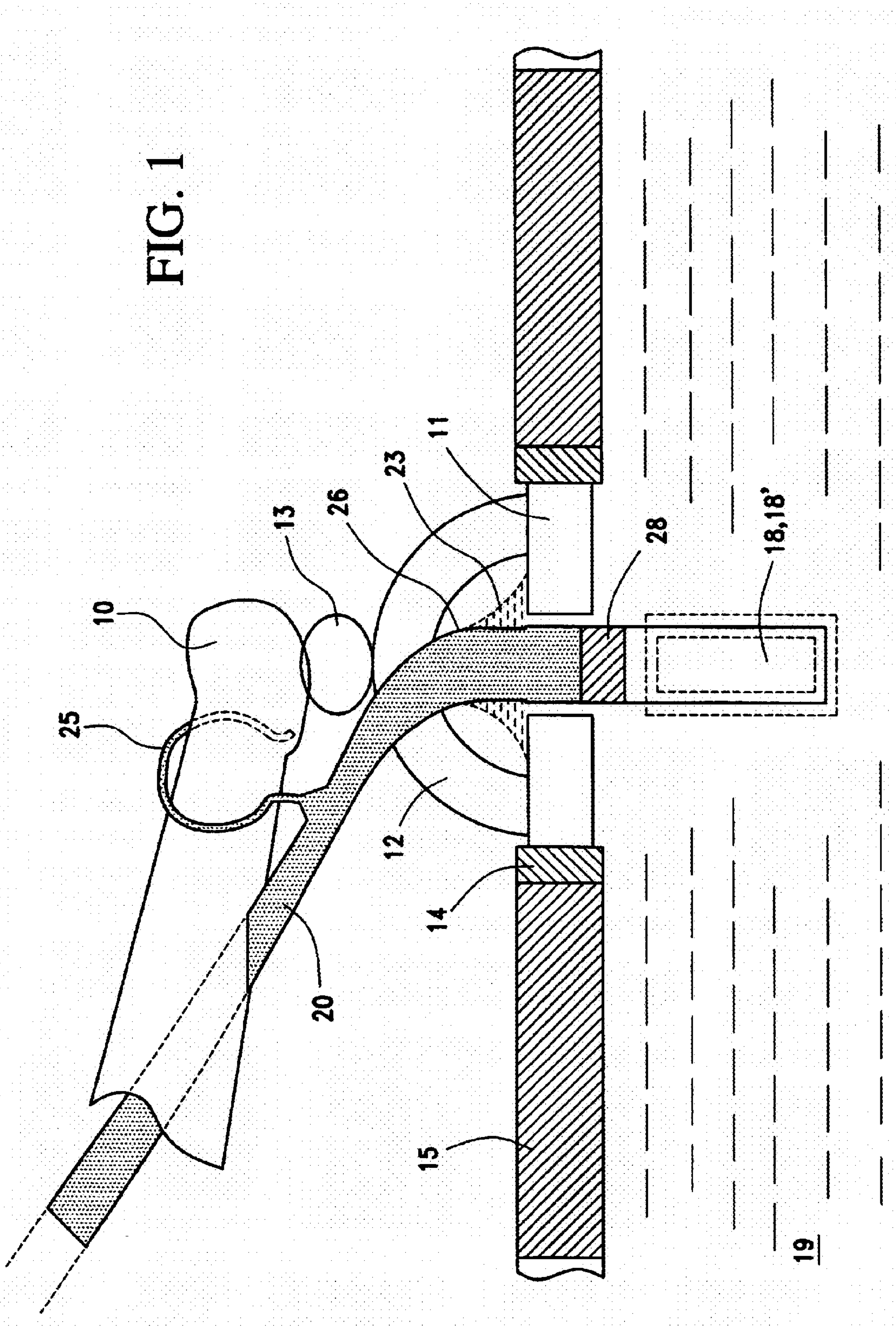
FIG. 1 shows a sectional view of a part of a human middle ear together with an implanted intracochlear transducer.

FIG. 1 schematically shows a sectional view of a part of a human middle ear including the long incus process 10, the stapes with the footplate 11 (presently illustrated in perforated form), the stapes upper structure (leg 12, head 13) and the ligament 14 by which the stapes is suspended in the oval window of the bony cochlear wall 15.

An intracochlear electromechanical transducer 18, 18' is introduced as a whole into the inner ear through a perforation of the footplate 11 of the stapes. The oscillations of the transducer 18, 18' indicated in FIG. 1 by interrupted lines result in dynamic volume displacements of perilymph 19 in the scala tympani of the inner ear. The transducer 18, 18' is connected to an implant feed line 20 which includes the electrical transducer leads 21 shown in FIG. 2. The implant feed line 20 preferably is sealed in the course of the operation within the perforation of the stapes footplate by being enclosed with fascia or another endogenic tissue 23 as this is known from stapes prosthetics. The line 20 may be fixed on the long incus process 10 by a deformable and preferably metallic hook or loop 25 which is known from stapes prosthetics. Basically, the implant line 20 and the attachment of transducer 18, 18' to the distal end of this line are designed as in the case of an intracochlear cochlea implant electrode. That means, a mechanical carrier 26 for the transducer 18, 18' is attached to the distal end of the implant line 20. This carrier preferably essentially consists of a flexible polymeric structural part which preferably has a circular cross-section.

Furthermore, a mechanical attenuation element 28 may be provided which element decouples the oscillations of transducer 18, 18' from feed line 20 and thus avoids or at least reduces a transmission of transducer oscillations to the middle ear ossicles, which transducer oscillations could result in undesired feedback when using a sound sensor (microphone) disposed in the vicinity of the ossicles.

Preferably, the operation of the electromechanical transducer 18, 18' is based on the principle of a dynamic volume change as a result of dynamic surface enlargement or reduction in conformity with an electrical AC signal controlling the transducer. The volumetrical changes required for an adequate sound pressure level of about 100 dB SPL amount to about $2 \cdot 10^{-4}$ microliters. The total diameter of the intracochlear transducer arrangement is within a range from 0.2 mm to 2.0 mm. The depth of immersion of the transducer is within a range from 0.3 mm to 2 mm, and the length of the active transducer element is in the same range.

Figure 2:
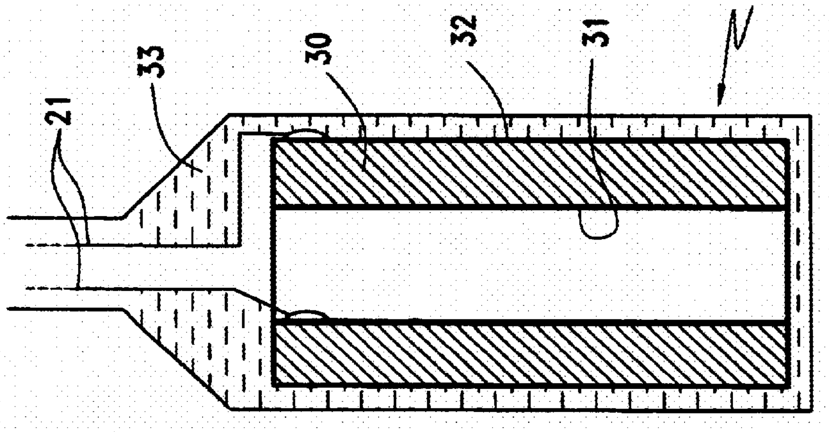
FIG. 2 shows the basic structure of the intracochlear transducer of FIG. 1.

FIG. 2 illustrates the basic structure of transducer 18 when a piezoelectric tube section 30, preferably made of lead-zirconate-titanate and having a cylindrical cross-section, is used. Metallic coatings are applied on the inner and outer circumferential surfaces of tube section 30, and these metal coatings define transducer electrodes 31 and 32. In conformity with a further preferred embodiment, the transducer also may be made of a single- or multi-layer coil of a thin polyvinylidene fluoride (PVDF) foil. The material of the metallic coatings consists of a biocompatible metal which preferably is selected from the group consisting of pure gold, platinum, platinum-iridium, titanium, tantalum, stainless steels, and biocompatible alloys thereof. The connection of the transducer electrodes 31 and 32 is effected via the two transducer leads 21. The material of these leads is selected from the materials indicated above for the metallic coatings.

The application of an electrical alternating voltage on the piezoelectric tube section 30 results in a corresponding dynamic change of the radius of the transducer what leads to the described dynamic volume displacement within the intracochlear liquid. In this embodiment the entire transducer element 30, 31, 32 preferably is enclosed by a thin biocompatible cover 33. Preferably, cover 33 is made of an elastic polymer, for example silicone which proved to be an excellent carrier material for cochlea implant electrodes.

Figure 4:
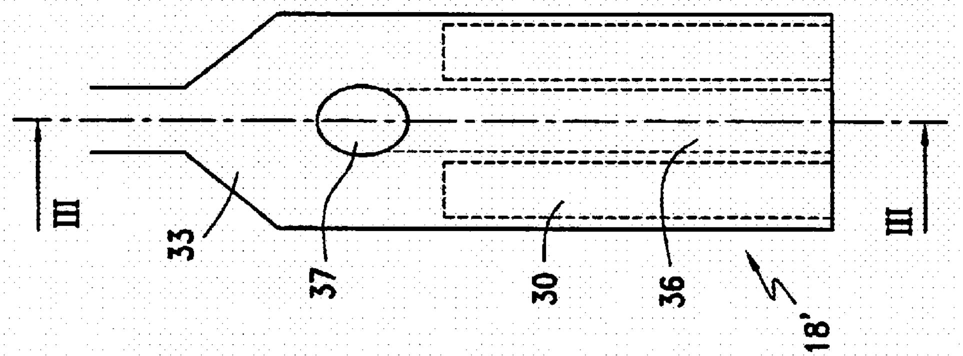
FIG. 4 is a side view of the intracochlear transducer according to FIG. 3.
Figure 3:
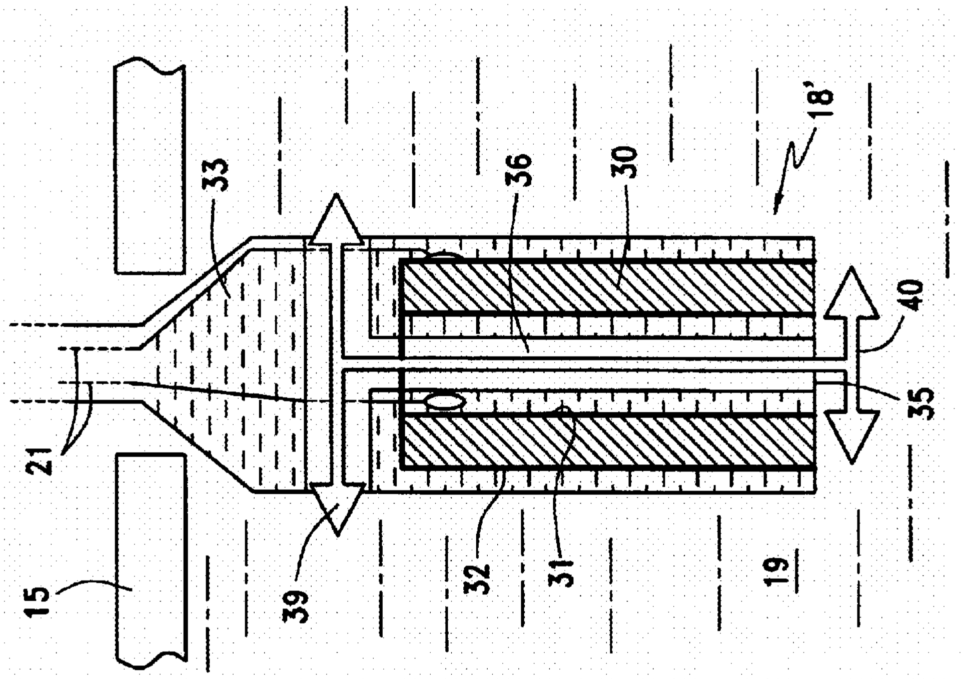
FIG. 3 is a sectional view of a modified embodiment of the intracochlear transducer of FIG. 1, taken along lines III—III of FIG. 4.

FIGS. 3 and 4 schematically illustrate a modified embodiment of the transducer of FIG. 2. In this embodiment the transducer 18' is not completely enclosed by the polymeric cover 33. Rather, entry and exit of intracochlear lymph into and out of the interior 36 of the tube is possible via an open lower end 35 of tube section 30 and via a transverse opening 37 which is disposed at the upper region of the cover 33, as this is indicated in FIG. 3 by arrows 39 and 40. The dynamic change of the radius of transducer 18' thus directly results in a displacement of lymph and therefore in an intracochlear volume displacement. By properly designing the tube surface and the cross-sectional area of the inlet and outlet openings 35, 37 a transformation according to the hydraulic principle can be attained, which leads to higher velocities of the displaced lymph and accordingly to higher levels of the stimulation of the cochlea than those obtained by a direct surface change of the transducer itself.

Figure 5:
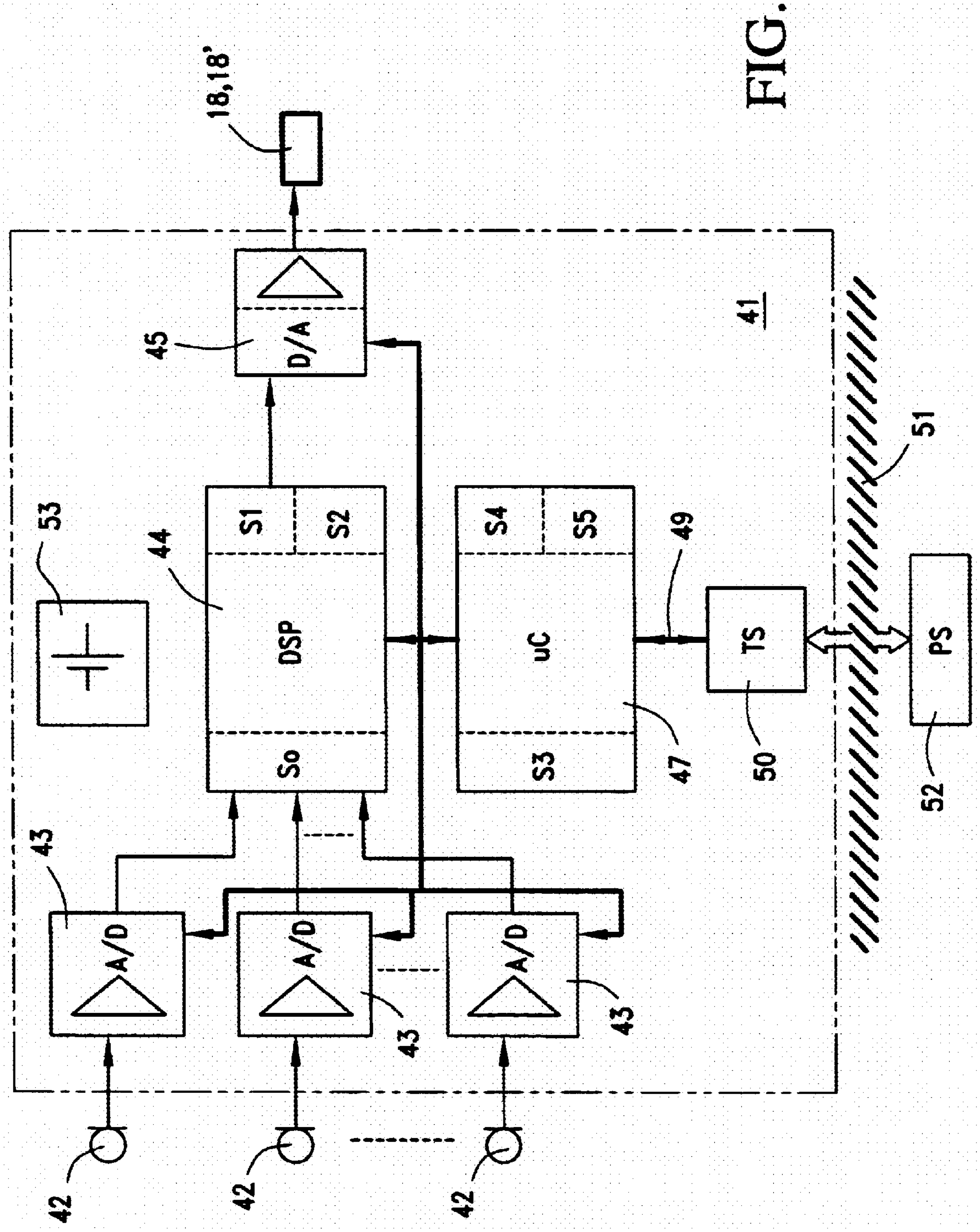
FIG. 5 is a block circuit diagram of a fully implantable hearing system for rehabilitation of a middle ear and/or inner ear hearing disorder and/or of a tinnitus.

FIG. 5 shows an embodiment of an electronic signal processing module 41 of the at least partially implantable hearing system according to the invention. One or more acoustic sensors (microphones 42) receive the sound signal and convert it into corresponding electrical signals. These sensor signals are selected, preprocessed and converted into digital signals (A/D conversion) in a unit 43. The preprocessing can consist, for example, of an analog linear or nonlinear preamplification and filtering (for example anti-aliasing filtering). The digitized sensor signal(s) is (are) supplied to a digital signal processor 44 (DSP) which executes the intended function of the hearing implant, for example, audio signal processing in a system for inner ear hearing disorders and/or signal generation in the case of a tinnitus masker or noiser. The signal processor 44 contains a read only memory area $S_0$ which cannot be overwritten and in which the instructions and parameters necessary for a "minimum operation" of the system are stored. The signal processor 44 also contains a storage area $S_1$ in which the operating software of the intended function or functions of the implant system is filed. Preferably, this storage area is present twice ($S_1$ and $S_2$). The rewritable program storage for holding the operating software can be based on EEPROM or RAM cells, and in this case provisions should be made for this RAM area to always be "buffered" by the power supply system.

The digital output signals of the signal processor 44 are converted in a digital to analog converter (D/A) and driver unit 45 into analog signals and are brought to the level desired for controlling the transducer 18, 18'. The unit 45 can be completely eliminated if, for example, in the case of a hearing system having an electromagnetic intracochlear output transducer, a pulse-width modulated, serial digital output signal of the signal processor 44 is transferred directly to the output transducer.

In the embodiment shown in FIG. 5, the signal processing components 43, 44 and 45 are controlled, via a bidirectional data bus 48, by a microcontroller 47 ($\mu$C) having one or two associated storages $S_4$ and $S_5$, respectively. In the storage area(s) $S_4$ and $S_5$, respectively, particularly the operating software portions of the implant management system can be filed, such as for example administration, monitoring and telemetry functions. Memories $S_1$ and/or $S_2$ can also file patient-specific parameters, for example audiological adaptation parameters, which can be altered from the outside. Furthermore, the microcontroller 47 has a rewritable storage $S_3$ in which a working program for the microcontroller 47 is filed.

The microcontroller 47 communicates in the illustrated implantable embodiment via a data bus 49 with a telemetry system 50 (TS). This in turn communicates bidirectionally wirelessly through the closed skin 51, by way of example via an inductive coil coupling not shown in FIG. 5, with an external programming system 52 (PS). The programming system 52 advantageously can be a PC-based system with corresponding programming, processing, display and administration software. The operating software of the implant system which is to be changed or completely replaced is transmitted via this telemetry interface, and at first is buffered in the storage area $S_4$ and/or $S_5$ of the microcontroller 47. The storage area $S_5$ may be used for example for complementary filing of the data transferred from the external system, and a simple verification of the software transmission by a reading operation may be carried out via the telemetry interface to check coincidence of the contents of storage areas $S_4$ and $S_5$ before changing or replacing the content of the rewritable storage $S_3$.

The operating software of the at least partially implantable hearing system presently is to be understood to include both the operating software of the microcontroller 47 (for example housekeeping functions such as energy management or telemetry functions) as well as the operating software of the digital signal processor 44. Thus, for example, simple verification of software transmission can be done by a reading process via the telemetry interface before the operating software, or the corresponding signal processing portions of this software, are transmitted into the program storage area $S_1$ of the digital signal processor 44 via the data bus 48. Furthermore, the working program for the microcontroller 47, stored for example in the rewritable storage $S_3$, can be changed or replaced in whole or in part via the telemetry interface 50 using the external unit 52.

All electronic components of the implant system are supplied with electrical operating energy by a primary or secondary battery 53.

Figure 6:
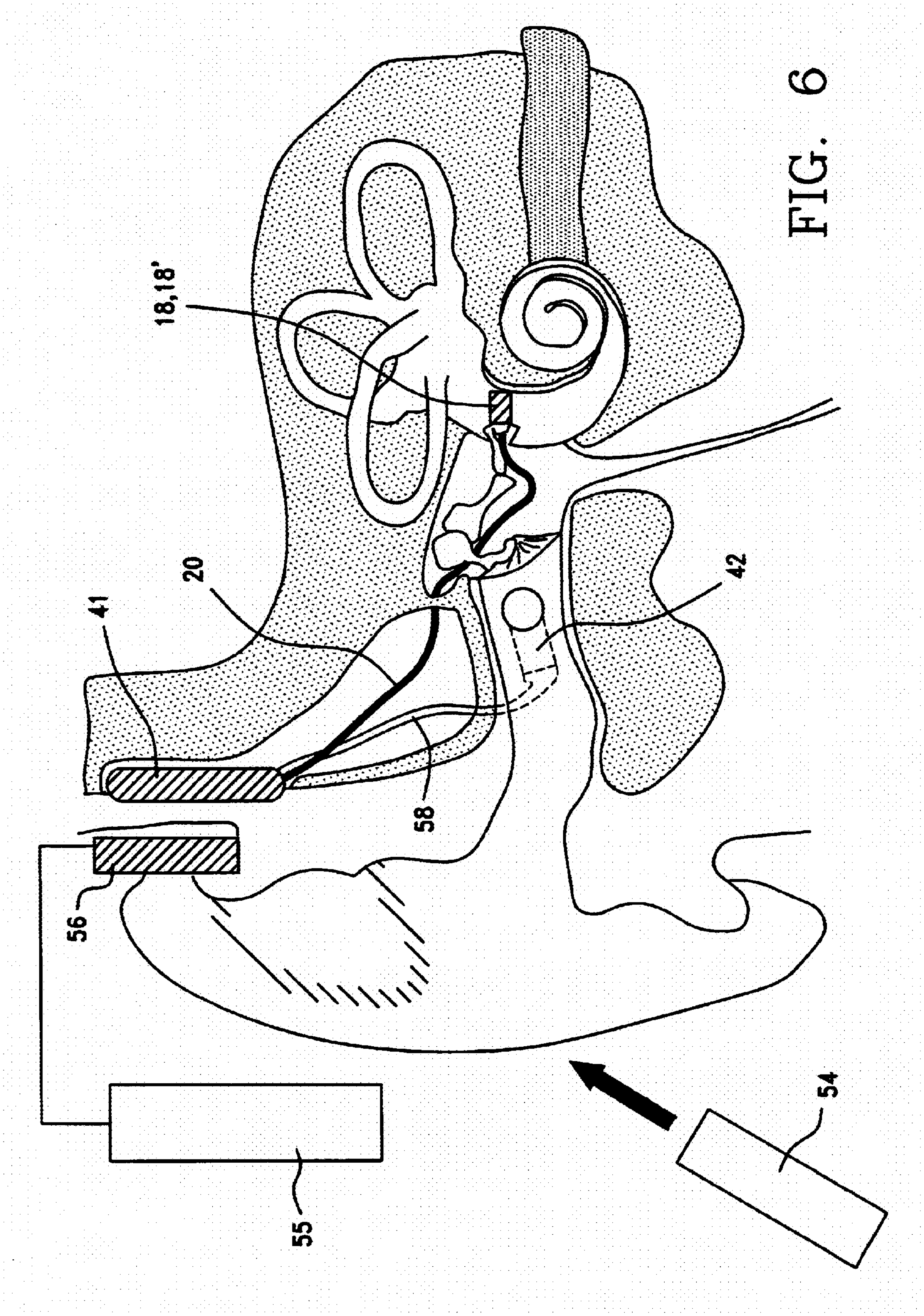
FIG. 6 shows an embodiment of a fully implantable hearing system in conformity with the invention.

FIG. 6 schematically shows an embodiment of a fully implantable hearing system comprising an intracochlear transducer 18 or 18' and an implantable microphone 42. A wireless remote control 54 is provided for control of the implant functions by the implant wearer. Furthermore the hearing system comprises a charging system comprising a charger 55 for wireless transcutaneous recharging of a secondary battery located in the implant for power supply of the hearing system, for example the battery 53 in FIG. 5.

The microphone 42 can advantageously be built in the manner known from commonly owned U.S. Pat. No. 5,814,095 which hereby is incorporated by reference. Particularly, microphone 42 can be provided with a microphone capsule which is accommodated hermetically sealed on all sides within a housing, and with an electrical feed-through connector for routing at least one electrical connection from within the housing to the outside thereof. The housing has at least two legs which are arranged at an angle relative to one another, a first one of the legs containing the microphone capsule and being provided with a sound inlet membrane, and a second one of the legs containing the electrical feed-through connector and being set back relative to the plane of the sound inlet membrane. The geometry of the microphone housing is chosen such that when the microphone is implanted in the mastoid cavity the leg which contains the sound inlet membrane projects from the mastoid into an artificial hole in the posterior bony wall of the auditory canal and the sound inlet membrane touches the skin of the wall of the auditory canal. To fix the implanted microphone 42, there can preferably be a fixation element of the type known from commonly owned U.S. Pat. No. 5,999,632 which hereby is incorporated by reference. This fixation element has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging system further includes a charging coil 56 connected to the output of the charging device 55. The charging coil 56 preferably forms part of a transmitting serial resonant circuit in the manner known from commonly owned U.S. Pat. No. 5,279,292 which hereby is incorporated by reference. The transmitting serial resonant circuit can be inductively coupled to a receiving serial resonant circuit which is not shown. In the embodiment of FIG. 6 the receiving serial resonant circuit can be part of the implantable electronic module 41, and, in conformity with U.S. Pat. No. 5,279,292, can form a constant current source for the battery 53. The receiving serial resonant circuit is connected in a battery charging circuit which, depending on the respective phase of the charging current flowing in the charging circuit, is closed via one branch or the other of a full wave rectifier bridge.

The electronic module 41 is connected in the arrangement as shown in FIG. 6 via a microphone line 58 to the microphone 42 and via the implant feed line 20 to the intracochlear transducer 18 or 18', respectively.

Figure 7:
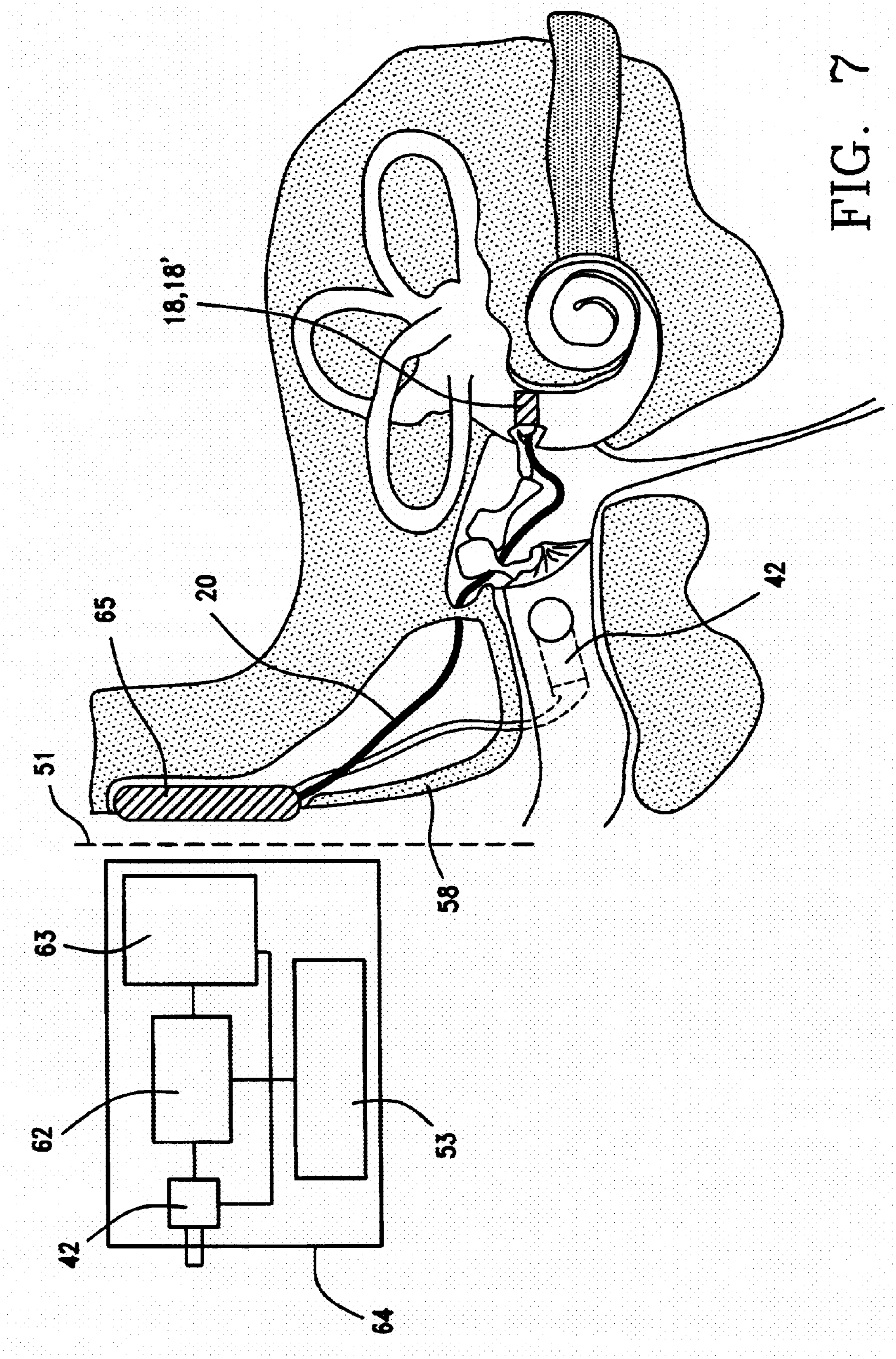
FIG. 7 shows an embodiment of a partially implantable hearing system in conformity with the invention.

FIG. 7 schematically shows the structure of a partially implantable hearing system comprising an intracochlear transducer 18 or 18', respectively, in conformity with FIGS. 1 to 4. This partially implantable system includes a microphone 42, an electronic module 62 for electronic signal processing for the most part according to FIG. 5 (but without the telemetry system 50), the power supply 53 and a modulator/transmitter unit 63 in an external module 64 which is to be worn externally on the body, preferably on the head over the implant. As in known partial implants, the implant is passive in terms of energy. Its electronic module 65 (without the battery 53) receives its operating energy and control signals for the transducer via the modulator/transmitter unit 63 in the external module 64.

Both the fully implantable hearing system and the partially implantable hearing system may be designed as a monaural system or as a binaural system. A binaural system for rehabilitation of a hearing disorder of both ears comprises a pair of system units, each of which units is associated to one of the two ears. Both system units may be essentially identical to one another. But one system unit can also be designed as a master unit and the other system unit as the slave unit which is controlled by the master unit. The signal processing modules of the two system units can communicate with one another in any way, especially via a wired implantable line connection or via a wireless connection, preferably a bidirectional high frequency path, a bodyborne sound-coupled ultrasonic path or a data transmission path which uses the electrical conductivity of the tissue of the implant wearer, such that in both system units optimized binaural signal processing is achieved.

Particularly, the following possibilities of combinations are possible:

Both electronic modules may each contain a digital signal processor according to the aforementioned description, and the operating software of the two processors can be transcutaneously changed, as described. Then the interconnection of the two modules provides essentially for data exchange for optimized binaural signal processing, for example, of the sensor signals.

Only one module contains the described digital signal processor. The module interconnection then provides, in addition to transmission of sensor data for binaural sound analysis and balancing, for transfer of the output signal to the contralateral transducer, wherein the latter module can house the electronic transducer driver. In this case, the operating software of the entire binaural system is filed in only one module, and the software also is changed transcutaneously only in this module from the outside via a telemetry unit which is present on only one side. In this case, the power supply of the entire binaural system can be housed in only one electronic module with power being supplied by wire or wirelessly to the contralateral module.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

I claim:

1. An at least partially implantable system for rehabilitation of a hearing order comprising:

at least one acoustic sensor for picking up acoustic sensor signals and converting the acoustic signals into corresponding electrical audio sensor signals, an electronic signal processing unit for audio signal processing and amplification of the electrical sensor signals, an electrical power supply unit which supplies individual components of the system with energy, and an actoric output arrangement for direct mechanical stimulation of a lymphatic inner ear space, wherein said actoric output arrangement comprises an intracochlear electromechanical transducer; wherein the intracochlear electromechanical transducer operates according the principle of dynamic volume change as a result of dynamic surface enlargement or reduction of the transducer in conformity with an electrical AC signal controlling the transducer; and wherein the transducer is a surface oscillator having a surface, at least a major portion of which is designed to oscillate in accordance with a dynamic volume change of the transducer.

2. The system as claimed in claim 1, wherein the intracochlear transducer approximates a ball-type oscillator.

3. The system as claimed in claim 1, wherein the intracochlear transducer is adapted for implantation using as an access the oval window or an artificial cochlear window.

4. The system as claimed in claim 1, wherein the intracochlear transducer is disposed at an end of a flexible carrier.

5. The system as claimed in claim 1, wherein the intracochlear transducer is a piezoelectric electromechanical transducer.

6. The system as claimed in claim 5, wherein the intracochlear piezoelectric transducer is made of a lead-zirconate-titanate material.

7. The system as claimed in claim 5, wherein the intracochlear piezoelectric transducer is made of a coil of polyvinylidene fluoride foil.

8. The system as claimed in claim 1, wherein the system has a transmission range and the intracochlear transducer has a first mechanical resonance frequency at the upper spectral end of the transmission range.

9. The system as claimed in claim 1, comprising a mechanical attenuation element for minimizing propagation of oscillations from the intracochlear transducer to a transducer feed line.

10. The system as claimed in claim 9, wherein the intracochlear transducer is disposed at an end of a flexible carrier and wherein the mechanical attenuation element is made of a material having a large mechanical impedance difference as compared to material of the carrier in order to achieve high attenuation values.

11. The system as claimed in claim 1, wherein the electronic signal processing unit comprises a digital signal processor which provides for at least one function selected from the group consisting of processing electrical audio sensor signals or generating digital signals for tinnitus masking.

12. The system as claimed is claim 11, wherein a rewritable implantable storage arrangement is assigned to the signal processor for storage and retrieval of an operating program, and wherein at least parts of the operating program are adapted to be at least partially replaced by data transmitted from an external unit via a telemetry means.

13. The system of claim 12, wherein the telemetry means is adapted for transmission of operating parameters between the implantable part of the system and the external unit.

14. The system of claim 12, further comprising a buffer storage arrangement in which data transmitted from the external unit via the telemetry means are buffered before being relayed to the signal processor.

15. The system of claim 14, wherein the buffer storage arrangement comprises at least two storage areas for storage and retrieval of data transferred from the external unit via the telemetry means.

16. The system of claim 14, further comprising a checking logic for checking data stored in the buffer storage arrangement before said data are relayed to the signal processor.

17. The system of claim 11, comprising a microprocessor module for control of the digital signal processor via a data bus.

18. The system of claim 17, wherein a checking logic and a buffer storage arrangement are implemented in the microprocessor module.

19. The system of claim 17, wherein at least one of a plurality of program parts are adapted to be transferred between an external source, the microprocessor module and the signal processor via the data bus and a telemetry means.

20. The system of claim 17, wherein an implantable storage arrangement for storage of an operating program for the microprocessor module is assigned to the microprocessor module, and at least one of a plurality of parts of the operating program for the microprocessor module is adapted to be replaced by data transferred from an external unit via a telemetry means.

21. The system of claim 11, comprising at least two storage areas for storage an retrieval of at least an operating program of the signal processor.

22. The system of claim 11, wherein a preprogrammed read-only memory area is assigned to the signal processor.

23. The system of claim 1, wherein the electrical power supply unit comprises an implantable rechargeable energy storage element, and wherein the system is totally implantable except for a wireless, transcutaneous charging device which is provided for charging of the energy storage element.

24. The system of claim 23, comprising a wireless remote control for control of implant functions by the implant wearer.

25. The system of claim 1, wherein the system is partially implantable, wherein said at least one acoustic sensor said electronic signal processing unit, said power supply unit and a modulator/transmitter unit are contained in an external module to be worn externally on the body of a user, and wherein the at least one electromechanical output transducer is an implantable passive unit which receives operating energy and control data for the transducer and a clutch via the modulator/transmitter unit in the external module.

26. An at least partially implantable system for rehabilitation of a hearing disorder comprising:

at least one acoustic sensor for picking up acoustic sensor signals and converting the acoustic sensor signals into corresponding electrical audio sensor signals, an electronic signal processing unit for audio signal processing and amplification of the electric sensor signals, an electrical power supply unit which supplies individual components of the system with energy, and an actoric output arrangement for direct mechanical stimulation of a lymphatic inner ear space, wherein said actoric output arrangement comprises an intracochlear electromechanical transducer; wherein the intracochlear transducer comprises a piezoelectric tube section having metal coatings on inner and outer circumferential surfaces thereof said metal coatings defining transducer electrodes.

27. An at least partially implantable system for rehabilitation of a hearing disorder comprising:

at least one acoustic sensor for picking up acoustic sensor signals and convening the acoustic sensor signals into corresponding electrical audio sensor signals, an electronic signal processing unit for audio signal processing and amplification of the electrical sensor signals, an electrical power supply unit which supplies individual components of the system with energy, and an actoric output arrangement for direct mechanical stimulation of a lymphatic inner ear space, wherein said actoric output arrangement comprises an intracochlear electromechanical transducer; wherein the intracochlear transducer is a piezoelectric electromechanical transducer; wherein the intracochlear piezoelectric transducer comprises a biocompatible cover having at least one opening for entry and exit of intracochlear lymph, and wherein a dynamic change of radius of the transducer directly results in an intracochlear displacement of lymph.

28. The system as claimed in claim 27, wherein the intracochlear transducer comprises a piezoelectric tube section having metal coatings on inner and outer circumferential surfaces thereof, said metal coatings defining transducer electrodes, and wherein openings for entry and exit of intracochlear lymph are provided at a free end of the tube section and in the cover at the side of the tube section remote from said free end thereof.

29. The system as claimed in claim 28, wherein the openings for entry and exit of intracochlear lymph have cross-sectional areas which, in relation to the surface area of the tube section, are dimensioned to provide for a hydraulic transformation such that higher lymph velocities and consequently higher cochlea stimulation levels are attained than those obtained by a direct surface change of the transducer itself.

* * * * *